US012752008B2

(12) United States Patent
Funase et al.

(10) Patent No.: US 12,752,008 B2
(45) **Date of Patent: *Oct. 6, 2026**

(54) COMPOSITION CONTAINING BUFFER

(71) Applicant: PERSEUS PROTEOMICS INC., Tokyo (JP)

(72) Inventors: Yuichi Funase, Ashigarakami-gun (JP); Masahiro Kurokawa, Sammu (JP)

(73) Assignee: PERSEUS PROTEOMICS INC., Tokyo (JP)

( * ) Notice: Subject to any disclaimer, the term of this patent is extended or adjusted under 35 U.S.C. 154(b) by 73 days.

This patent is subject to a terminal disclaimer.

(21) Appl. No.: 18/438,751

(22) Filed: Feb. 12, 2024

(65) Prior Publication Data

US 2024/0245777 A1 Jul. 25, 2024

Related U.S. Application Data

(62) Division of application No. 16/321,973, filed as application No. PCT/JP2017/029696 on Aug. 21, 2017, now Pat. No. 11,951,168.

(30) Foreign Application Priority Data

Aug. 19, 2016 (JP) ................................ 2016-161114

(51) Int. Cl.

| | |
|---|---|
| ***A61K 47/12*** | (2006.01) |
| ***A61K 33/24*** | (2019.01) |
| ***A61K 33/244*** | (2019.01) |
| ***A61K 47/18*** | (2017.01) |
| ***A61K 47/50*** | (2017.01) |
| ***A61K 51/00*** | (2006.01) |
| ***A61K 51/04*** | (2006.01) |
| ***A61P 35/00*** | (2006.01) |
| ***A61P 35/02*** | (2006.01) |
| *A61K 9/00* | (2006.01) |
| *A61K 51/12* | (2006.01) |

(52) U.S. Cl.

CPC .............. *A61K 47/12* (2013.01); *A61K 33/24* (2013.01); *A61K 33/244* (2019.01); *A61K 47/18* (2013.01); *A61K 47/50* (2017.08); *A61K 51/00* (2013.01); *A61K 51/048* (2013.01); *A61K 51/0482* (2013.01); *A61P 35/00* (2018.01); *A61P 35/02* (2018.01); *A61K 9/0019* (2013.01); *A61K 51/1241* (2013.01)

(58) Field of Classification Search

CPC ........ A61K 47/12; A61K 47/18; A61K 47/50; A61K 51/00; A61P 35/00

See application file for complete search history.

(56) References Cited

U.S. PATENT DOCUMENTS

| | | | | |
|---|---|---|---|---|
| 2005/0215472 A1* | 9/2005 | Schulke | A61K 47/6825 | 514/19.5 |
| 2011/0286920 A1 | 11/2011 | Jeong | | |
| 2012/0009124 A1 | 1/2012 | Port. et al. | | |
| 2012/0128584 A1* | 5/2012 | Togashi | G01N 33/57557 | 424/1.49 |
| 2013/0071324 A1 | 3/2013 | Hino et al. | | |
| 2015/0132219 A1* | 5/2015 | Kjaer | C12N 9/6456 | 424/1.69 |
| 2016/0137730 A1 | 5/2016 | Abrams | | |

FOREIGN PATENT DOCUMENTS

| | | | |
|---|---|---|---|
| CN | 102341127 | A | 2/2012 |
| CN | 105617413 | A | 6/2016 |
| DE | 103 61 598 | A1 | 7/2005 |
| DE | 10 2004 014 783 | A1 | 10/2005 |
| JP | 2012-517974 | A | 8/2012 |
| WO | WO 2011 /099524 | A | 8/2011 |

OTHER PUBLICATIONS

Sandeep Nema et al. Excipeints and Their Role in Approved Injectable PRoducts: Current Usage and Future Directions, PDA J Pharm Sci and Tech, 65, 287-332. (Year: 2011).*

International Search Report issued Nov. 21, 2017 in PCT/JP2017/029696 filed Aug. 21. 2017.

Allan, K. F. et al., "Separation of 153Sm from Other Rare-Earth Radionuclides Present in Neutron-Irradiated Samarium Oxide Target Using Polymeric Resin," Radiochemistry, vol. 51, No. 5, 2009, pp. 502-506.

Liu, S. "Bifunctional coupling agents for radiolabeling of biomolecules and target-specific delivery of metallic radionuclides," Advanced Drug Delivery Reviews, vol. 60, 2008, pp. 1347-1370.

Extended European Search Report issued on Mar. 18, 2020 in European Patent Application No. 17841575.8, 10 pages.

David Parker, et al., "Implementation of Macrocycle Conjugated Antibodies for Tumour-Targetting" Pure & Applied Chemistry, vol. 61, No. 9, XP000256650, Jan. 1, 1989, pp. 1637-1641.

Combined Chinese Office Action and Search Report Issued January 6, 202, in Chinese Paten! Application No. 201780050768. 1 (with English transla1lon of Summary of Office Action and English translation of Category of Cited Documents) 14 pages.

Denardo et al., (1998) Clin Cancer Res. 4(10):2483-90 (Year: 1998).

Peterson et al., (1999) Bioconjug. Chem. 10(4):553-7 (Year: 1999).

Zimmerman et al., (1999) Nucl. Med. Biol. 26(8):943-50 (Year: 1999).

* cited by examiner

*Primary Examiner* — Michael G. Hartley
*Assistant Examiner* — Jagadishwar R Samala
(74) *Attorney, Agent, or Firm* — Oblon, McClelland, Maier & Neustadt, L.L.P.

(57) ABSTRACT

Provided is a composition containing a buffer to be used at the time of labeling of a chelated targeting agent with $^{90}Y$, $^{153}Sm$, $^{165}Dy$, $^{165}Er$, $^{166}Ho$, or $^{177}Lu$. At least one kind of buffer selected from the group consisting of benzoic acid, maleic acid, fumaric acid, succinic acid, and salts thereof is incorporated in a composition containing a chelated targeting agent.

12 Claims, No Drawings

COMPOSITION CONTAINING BUFFER

This application is a divisional of U.S. application Ser. No. 16/321,973 filed Jan. 30, 2019, pending, which is a 371 application of PCT/JP2017/029696, filed Aug. 21, 2017 and claims the benefit of Japanese Application No. 2016-161114, filed Aug. 19, 2016. The contents of each of these applications are incorporated herein by reference in their entirety.

TECHNICAL FIELD

The present invention relates to a composition containing a buffer for preparing a radioactive metal-labeled chelated targeting agent.

BACKGROUND ART

Radiopharmaceuticals used in the field of nuclear medicine each have a form called a kit or a form called an injection. The kit involves a composition for causing a radioactive metal and a chelated targeting agent to react with each other to prepare an injection to be administered to a human in a medical setting, and is formed of at least the radioactive metal and the chelated targeting agent stored separately from the radioactive metal. Meanwhile, the injection involves a composition prepared so as to be able to be administered as it is in the medical setting.

The radioactive metal constituting the kit is generally supplied as a hydrochloric acid solution having a pH of around 1. For example, an appropriate amount of hydrochloric acid is added as an additive to $^{111}$In or $^{90}$Y constituting a kit of Zevalin (trademark) serving as a RI-labeled antibody therapeutic drug. Many other radioactive metals are supplied as hydrochloric acid solutions.

The chelated targeting agent is a conjugate of a chelate group and a targeting moiety. The chelated targeting agent is labeled with the radioactive metal by forming a complex between the chelate group and the radioactive metal. For example, ibritumomab tiuxetan under the trade name of Zevalin (trademark) is a chelated targeting agent, and is a conjugate of a targeting moiety called ibritumomab serving as an anti-CD20 antibody and a chelate group called tiuxetan or MX-DTPA. Ibritumomab tiuxetan is used after labeled with $^{111}$In or $^{90}$Y.

A reaction between the chelate group and the radioactive metal often occurs in a weakly acidic or neutral aqueous solution. In order to adjust a pH in such labeling reaction, the kit generally further contains a buffer. The kit is designed so that the buffer neutralizes hydrochloric acid in which the radioactive metal is dissolved, and adjusts the pH to a pH optimal to the reaction. Zevalin (trademark) contains sodium acetate as a buffer.

In addition, as an example using an acetate buffer, the applicant disclosed a radioactive metal-labeled anti-cadherin antibody obtained by labeling an anti-cadherin antibody with $^{67}$Ga, $^{111}$In, or $^{90}$Y in the presence of an acetate buffer (ammonium acetate-HCl) (Patent Literature 1).

As described above, the acetate buffer is a buffer which is most widely utilized in labeling with the radioactive metal. However, the acetate buffer has an acid dissociation constant (pKa) of 4.76, and hence has a limited buffering capacity covering only a pH range around the acid dissociation constant.

Under the above-mentioned background, in Patent Literature 2, a method for complexation of a chelate with gallium is investigated. It is disclosed that a chelate is completely complexed with gallium when a buffer selected from lactate, tartrate, carbonate, phosphate, ascorbate, succinate, and maleate buffers is used, but the chelate is not completely complexed with gallium when a citrate buffer is used. In addition, Octreoscan (trademark), which is a kit used for diagnosis of a neuroendocrine tumor, is formed of $^{111}$In and pentetreotide, and further contains citric acid and sodium citrate as a buffer. As described above, in the complexation of a chelate with a radioactive metal, the citrate buffer is not suitable for gallium, but is suitable for indium. It is indicated that some buffers are suitable for a certain radioactive metal but other buffers are not suitable for the radioactive metal.

In addition, the kit adopts a form of a freeze-dried formulation in some cases, but the acetate buffer, which is widely used, sublimates in the course of freeze-drying, and hence cannot be selected as the buffer.

CITATION LIST

Patent Literature

Patent Literature 1: JP-A-2011-99524
Patent Literature 2: JP-A-2012-517974

SUMMARY OF THE INVENTION

Problems to be Solved by the Invention

As described above, it is not clarified what buffer can be used in the case of $^{90}$Y, $^{153}$Sm, $^{165}$Dy, $^{165}$Er, $^{166}$Ho, or $^{177}$Lu, and whether the buffer can be used for a freeze-dried formulation.

Thus, an object of the present invention is to provide a composition containing a novel buffer to be used at the time of labeling of a chelated targeting agent with $^{90}$Y, $^{153}$Sm, $^{165}$Dy, $^{165}$Er, $^{166}$Ho, or $^{177}$Lu.

In addition, another object of the present invention is to provide a freeze-dried composition containing a novel buffer to be used at the time of labeling of a chelated targeting agent with $^{90}$Y, $^{153}$Sm, $^{165}$Dy, $^{165}$Er, $^{166}$Ho, or $^{177}$Lu.

In addition, still another object of the present invention is to provide a method of producing a radioactive metal-labeled chelated targeting agent, comprising labeling a chelated targeting agent with $^{90}$Y, $^{153}$Sm, $^{165}$Dy, $^{165}$Er, $^{166}$Ho, or $^{177}$Lu in the presence of a novel buffer.

Means for Solving the Problems

In view of the foregoing, the inventors of the present invention made investigations into a labeling reaction with $^{90}$Y using various buffers, and as a result, found that at least one kind of compound selected from the group consisting of benzoic acid, maleic acid, fumaric acid, succinic acid, and salts thereof is effective as a buffer. Thus, the present invention was completed.

That is, the present invention provides the following items [1] to [13].

[1] A composition, comprising:

(a) a chelated targeting agent which is a conjugate of a chelate group and a targeting moiety; and (b) at least one kind of buffer selected from the group consisting of benzoic acid, maleic acid, fumaric acid, succinic acid, and salts thereof, the composition being used for forming a complex between a radioactive metal selected from the group consisting of $^{90}$Y, $^{153}$Sm, $^{165}$Dy, $^{165}$Er, $^{166}$Ho, and $^{177}$Lu and the chelated targeting agent.

[2] The composition according to [1], wherein the radioactive metal is selected from the group consisting of $^{90}Y$ and $^{177}Lu$.

[3] The composition according to [1] or [2], wherein the chelate group comprises a chelate group having a DOTA structure, a DTPA structure, or a NETA structure.

[4] The composition according to any one of [1] to [3], wherein the chelate group is selected from the group consisting of the following chelate groups:

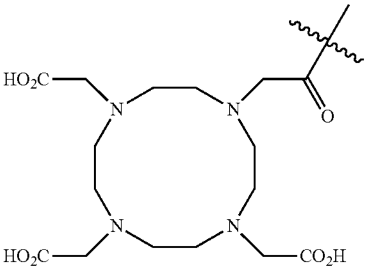

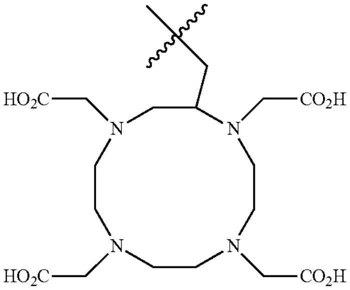

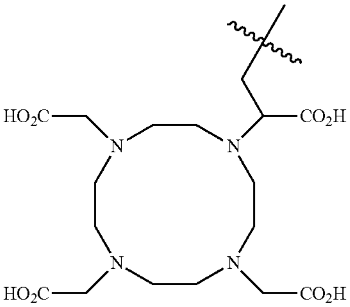

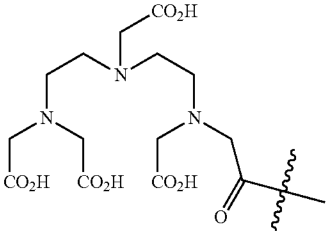

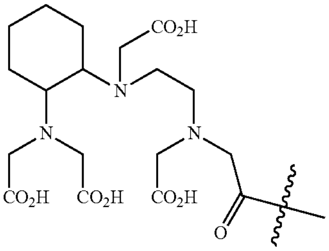

-continued

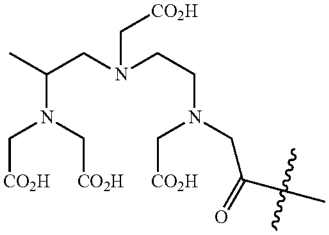

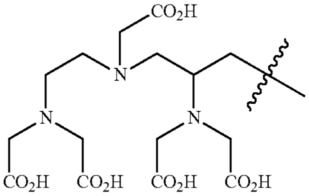

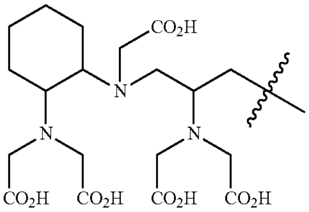

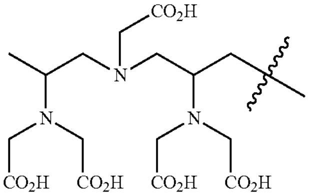

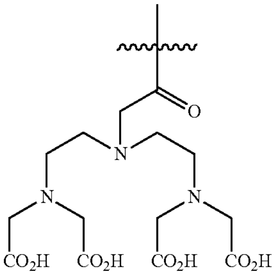

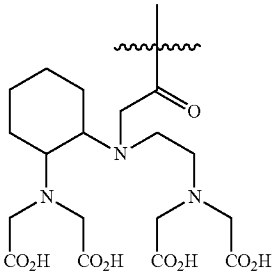

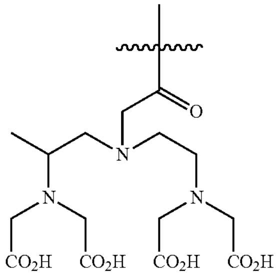

-continued

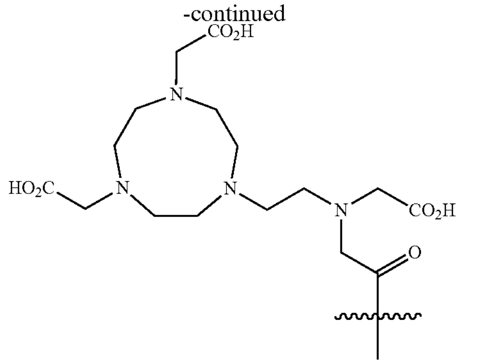

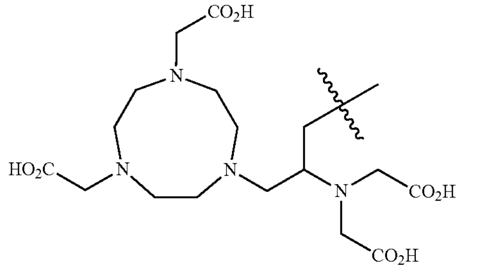

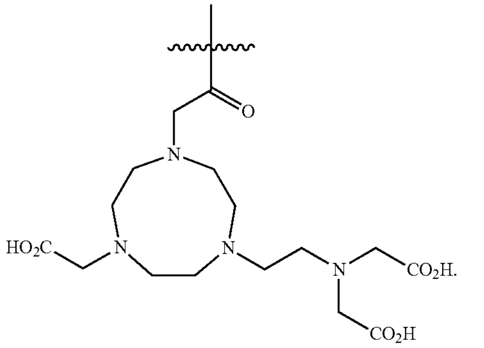

[5] The composition according to any one of [1] to [4], wherein the targeting moiety is selected from the group consisting of a low-molecular-weight compound, a peptide, a protein, an antibody, an antibody fragment, and a nucleic acid.

[6] The composition according to any one of [1] to [5], wherein the chelated targeting agent and the buffer are stored in a same vessel.

[7] The composition according to any one of [1] to [6], wherein the buffer is freeze-dried.

[8] The composition according to any one of [1] to [7], further comprising a radioactive metal selected from the group consisting of $^{90}Y$, $^{153}Sm$, $^{165}Dy$, $^{165}Er$, $^{166}Ho$, and $^{177}Lu$, the radioactive metal and the chelated targeting agent being housed under a state in which the radioactive metal and the chelated targeting agent are prevented from being brought into contact with each other.

[9] A method of producing a radioactive metal-labeled chelated targeting agent, comprising:

mixing a radioactive metal selected from the group consisting of $^{90}Y$, $^{153}Sm$, $^{165}Dy$, $^{165}Er$, $^{166}Ho$, and $^{177}Lu$ and a chelated targeting agent in the presence of at least one kind of buffer selected from the group consisting of benzoic acid, maleic acid, fumaric acid, succinic acid, and salts thereof to form a complex between the radioactive metal and the chelated targeting agent.

[10] A drug for diagnosis or treatment of a disease, comprising a combination of: (A) a radioactive metal selected from the group consisting of $^{90}Y$, $^{153}Sm$, $^{165}Dy$, $^{165}Er$, $^{166}Ho$, and $^{177}Lu$; (B) a chelated targeting agent; and (C) at least one kind of buffer selected from the group consisting of benzoic acid, maleic acid, fumaric acid, succinic acid, and salts thereof, the disease being targeted by the chelated targeting agent.

[11] Use of a combination of: (A) a radioactive metal selected from the group consisting of $^{90}Y$, $^{153}Sm$, $^{165}Dy$, $^{165}Er$, $^{166}Ho$, and $^{177}Lu$; (B) a chelated targeting agent; and (C) at least one kind of buffer selected from the group consisting of benzoic acid, maleic acid, fumaric acid, succinic acid, and salts thereof, for producing a drug for diagnosis or treatment of a disease, the disease being targeted by the chelated targeting agent.

[12] A combination of: (A) a radioactive metal selected from $^{90}Y$, $^{153}Sm$, $^{165}Dy$, $^{165}Er$, $^{166}Ho$, and $^{177}Lu$; (B) a chelated targeting agent; and (C) at least one kind of buffer selected from benzoic acid, maleic acid, fumaric acid, succinic acid, and salts thereof, for use in diagnosing or treating a disease, the disease being targeted by the chelated targeting agent.

[13] A method of diagnosing or treating a disease, comprising administering a combination of: (A) a radioactive metal selected from the group consisting of $^{90}Y$, $^{153}Sm$, $^{165}Dy$, $^{165}Er$, $^{166}Ho$, and $^{177}Lu$; (B) a chelated targeting agent; and (C) at least one kind of buffer selected from the group consisting of benzoic acid, maleic acid, fumaric acid, succinic acid, and salts thereof, the disease being targeted by the chelated targeting agent.

Effects of the Invention

The composition of the present invention is useful as a composition for preparing a radioactive metal-labeled chelated targeting agent because the buffer contained in the composition exhibits a pH buffering action in a labeling reaction of the chelated targeting agent with the radioactive metal without disturbing the reaction.

In addition, the composition of the present invention is useful as a freeze-dried formulation because the buffer contained in the composition does not sublimate in the course of freeze-drying.

In addition, the production method of the present invention is useful as a method of producing a radioactive metal-labeled chelated targeting agent because of comprising using the buffer which exhibits a pH buffering action in a labeling reaction of the chelated targeting agent with the radioactive metal without disturbing the reaction.

In addition, the composition of the present invention is useful as a drug for diagnosis or treatment of a disease targeted by the chelated targeting agent.

Modes for Carrying Out the Invention

The present invention is described in detail below.

A buffer is a compound having an action of moderating a change in pH when an acid or a base is added, that is, having a buffering action. Examples of the buffer may include a mixture of a weak acid and a conjugate base thereof, and a mixture of a weak base and a conjugate acid thereof. However, the buffer only needs to become such mixture when dissolved in a medium. For example, when only a weak acid is dissolved in water, the weak acid becomes a mixture of the weak acid and a conjugate base thereof through acid dissolution equilibrium. Therefore, a case in which the buffer is formed of one kind of reagent is also encompassed in the present invention.

The buffer of the present invention is at least one kind selected from the group consisting of benzoic acid, maleic acid, fumaric acid, succinic acid, and salts thereof. Examples of the salts include alkali metal salts, such as a sodium salt and a potassium salt, alkaline earth metal salts, such as a calcium salt and a magnesium salt, and an ammonium salt. The buffer is preferably at least one kind selected from the group consisting of benzoic acid, maleic acid, succinic acid, and salts thereof, and is more preferably at least one kind selected from the group consisting of benzoic acid and salts thereof.

In order to adjust a pH to a target pH, it is appropriate to mix a weak acid and a salt of a conjugate base thereof, or mix the weak acid or the salt of a conjugate base thereof with a pH adjuster described below. It is preferred to select a buffer having a pKa close to a target reaction pH from the viewpoint of a buffering capacity. When a composition of the present invention is made into a radioactive metal-labeled chelated targeting agent, a solution of the composition has a pH of preferably 2 or more and 8 or less, more preferably 3 or more and 7 or less, even more preferably 4 or more and 6 or less.

A targeting moiety of a chelated targeting agent means a compound having a function of being selectively incorporated in a target site of a human body or being localized in the target site. In diagnosis or treatment of a disease, a compound which targets a molecule or an environment specific to the disease, and has specificity thereto is often selected as the targeting moiety. The targeting moiety is not limited by the mechanism for localization, and examples thereof include: an antibody or an antibody fragment binding to an antigen; an agonist or an antagonist binding to a receptor; an aptamer binding to a protein; a high-molecular-weight compound, such as a liposome, a micelle, or a carbon nanotube, each utilizing an EPR effect; and a low-molecular-weight compound, such as a nitroimidazole compound, accumulating in a hypoxic site.

The targeting moiety may be synthetic or natural, and a molecular weight thereof is also not limited. Specific examples thereof include a low-molecular-weight compound, a peptide including a linear one, a circular one, and a combination thereof, a protein, an antibody, an antibody fragment, a growth factor, an affibody, a unibody, a nanobody, a monosaccharide, a polysaccharide, a vitamin, a nucleic acid, a peptide nucleic acid, an aptamer, a liposome, a micelle, and a carbon nanotube.

When the targeting moiety is an antibody or an antibody fragment, the targeting moiety refers to a polyclonal antibody, a monoclonal antibody, a chimera antibody, a humanized antibody, a human antibody, or fragments thereof. The antibody fragment refers to a Fab fragment or a $F(ab')_2$ fragment.

The targeting moiety is preferably an anti-CDH3 antibody (anti-P-cadherin antibody), and is more preferably an anti-CDH3 antibody described in Patent Literature 1. Examples of the anti-CDH3 antibody include antibodies produced from cell lines PPMX2016, PPMX2025, PPMX2029, PPAT-052-02, PPAT-052-03, PPAT-052-09, PPAT-052-24, PPAT-052-25, PPAT-052-26, PPAT-052-28, PPAT-052-02c, PPAT-052-03c, PPAT-052-09c, PPAT-052-21c, PPAT-052-24c, PPAT-052-25c, PPAT-052-26c, PPAT-052-27c, PPAT-052-28c, and PPAT-052-29c.

A radioactive metal means a nuclide which is a metal element and is a radioactive nuclide.

The radioactive metal of the present invention is selected from the group consisting of $^{90}Y$, $^{153}Sm$, $^{165}Dy$, $^{165}Er$, $^{166}Ho$, and $^{177}Lu$. Sm, Dy, Er, Ho, and Lu are called lanthanoids, belong to rare earth elements together with Y, and have common physical and chemical properties. Those elements each prefer a trivalent oxidized state, and have close ionic radii through lanthanoid contraction. Accordingly, Y and the lanthanoids are in a relationship of being treated equally with each other in coordination chemistry, and being similar to each other (Liu et al., Advanced Drug Delivery Reviews 60: 1347-1370 (2008)). The radioactive metal of the present invention is preferably $^{90}Y$ or $^{177}Lu$, and is more preferably $^{90}Y$.

A chelate group means an organic group which can be chelated with the radioactive metal. Specific examples thereof include chelate groups having, as a basic skeleton, a 1,4,7,10-tetraazacyclododecane-1,4,7,10-tetraacetic acid (DOTA) structure, a diethylenetriaminepentaacetic acid (DTPA) structure, and a [2-(4,7-biscarboxymethyl[1,4,7]triazacyclononan-1-yl-ethyl)carbonylmethylamino)acetic acid (NETA) structure. NETA is a chelate devised in expectation of having combination performance of the following two features: high complex stability, which is a feature of DOTA; and a high complexation speed, which is a feature of DTPA, and is known to have a higher complexation speed with Y than DOTA (Chong et al., Journal of Medicinal Chemistry 45: 3458-3464 (2002)). In each of those basic skeletons, a carboxyl group may be used for an amide bond with the targeting moiety. The DOTA structure, the DTPA structure, and the NETA structure each coordinate with Y or the lanthanoids through an amino group and a carboxyl group, and a carbonyl group of an arbitrary amide to form a stable complex. In addition, in each of those basic skeletons, one of ethylene groups may be a cyclohexylene group or an isopropylene group. In addition, the chelate group is conjugated to the targeting moiety through a carboxyl group or a side chain introduced into an ethylene group or a methylene group of each of the basic skeletons. Such side chain is preferably a side chain which enables easy conjugation of the chelate group to the targeting moiety, and groups having active groups, such as an anhydride group, a bromoacetamide group, an iodoacetamide group, an isothiocyanate group, an isothiocyanatobenzyl group, an N-hydroxysuccinimide group, and a maleimide group, are known (Liu et al., Advanced Drug Delivery Reviews 60: 1347-1370 (2008)).

The chelate group of the present invention is preferably a chelate group having the DOTA structure, the DTPA structure, or the NETA structure, and is more preferably a chelate group represented by any one of the following formulae.

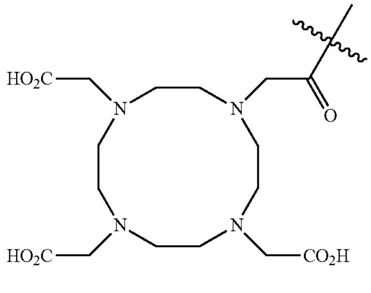

-continued
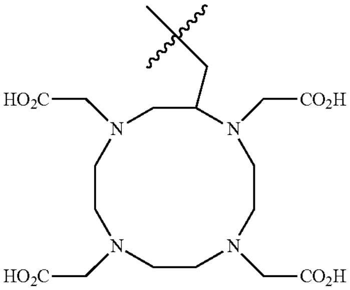
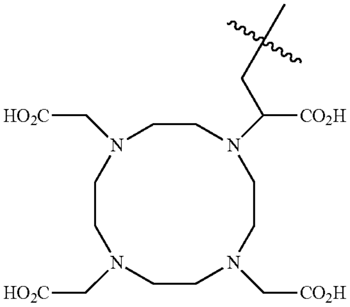
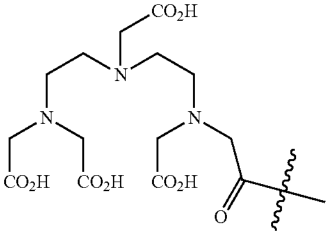
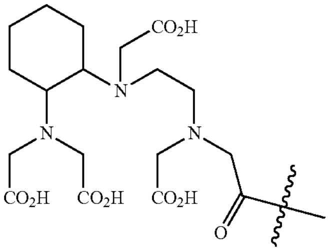
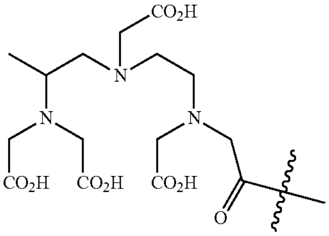
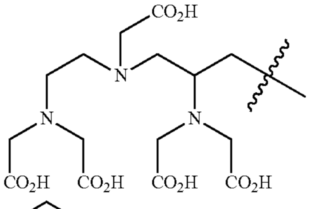
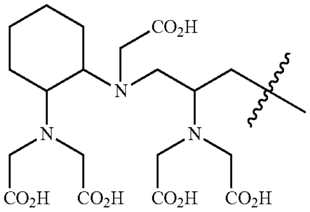
-continued
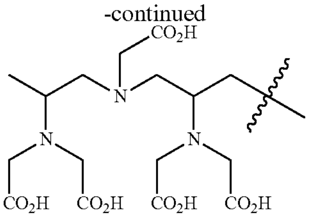
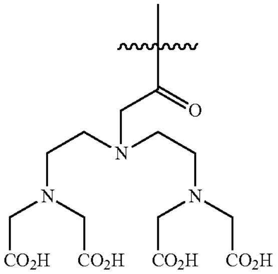
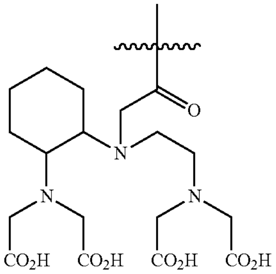
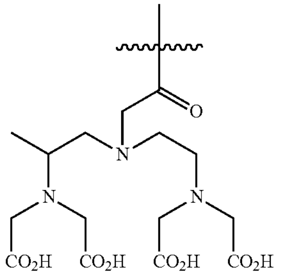
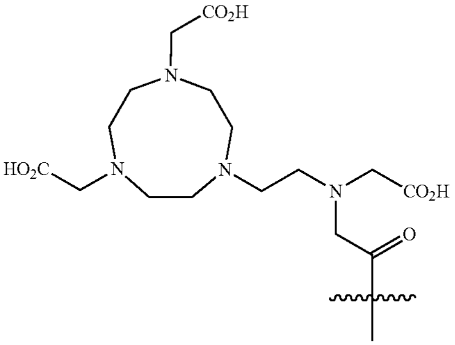
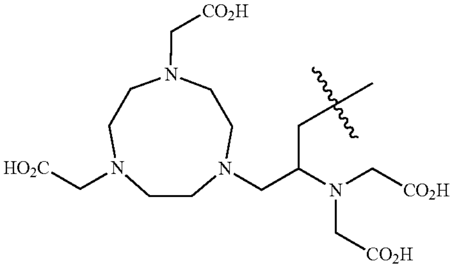
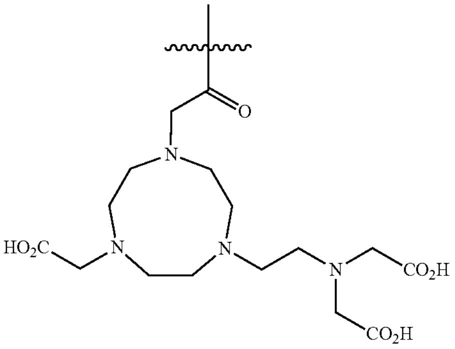

The chelate group of the present invention is even more preferably a chelate group represented by any one of the following formulae.

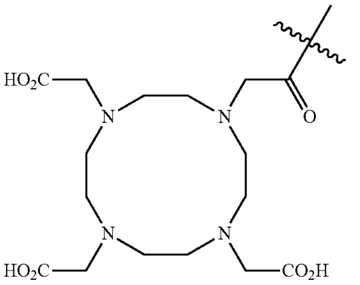

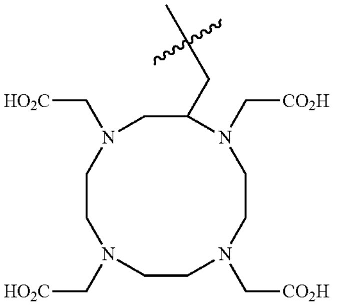

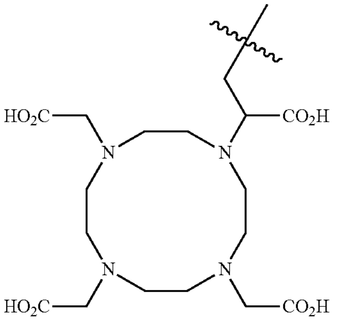

A chelated targeting agent means a conjugate in which the chelate group and the targeting moiety are conjugated to each other through a covalent bond. Each of the above-mentioned groups having active groups is commonly used for the conjugation. At the time of conjugation, a group called a linker, a spacer, or the like may be appropriately sandwiched between the chelate group and the targeting moiety, and for example, linkers of various types are given in Patent Literature 1. The linker is used to control a charge, lipophilicity, and hydrophilicity so that in vivo distribution of the targeting moiety is optimized, and also serves to prevent a bulky complex from sterically disturbing binding of the targeting moiety to a target in vivo.

Freeze-drying means a technology involving removing water from a frozen composition through sublimation under a vacuum environment. The buffer of the present invention does not sublimate through freeze-drying, and hence can also be utilized for a freeze-dried formulation. The freeze-drying is commonly used particularly in the field of treating a protein as a method for solving problems derived from physical instability, such as denaturation or aggregation, and chemical instability, such as deamidation or oxidation, and can prolong a shelf life of the composition. Accordingly, when the chelated targeting agent of the present invention is a protein, a freeze-dried formulation in which the chelated targeting agent and the buffer are stored in the same vessel is preferred. The composition of the present invention may be in a state of being freeze-dried. Specifically, when the composition of the present invention having added thereto water is freeze-dried, the composition of the present invention can be put into a state of being freeze-dried.

The effective content of the buffer is preferably such an amount that, when the buffer is mixed with a radioactive metal-containing solution, the buffer can neutralize an acid contained in the solution and can maintain an optimal reaction pH. The radioactive metal is reduced in amount from moment to moment in accordance with a half-life thereof, and hence the amount of the radioactive metal required at the time of preparation of an injection is calculated backward from administration time to a human. That is, in general, the amount of the radioactive metal-containing solution to be used at the time of preparation of the injection is not constant. Accordingly, the content of the buffer is preferably set to an amount capable of responding to the maximum assumable amount of the radioactive metal-containing solution, and the buffer may be used in the entire amount or in a variable amount in accordance with the amount of the radioactive metal-containing solution at the time of preparation of the injection. The content of the buffer is not particularly limited as long as a reaction pH can be adjusted to fall within a target pH range, but is preferably such an amount that a pH of a reaction liquid at the time of labeling of the chelated targeting agent with the radioactive metal is adjusted to fall within a range of preferably the pKa value of the buffer to be used plus or minus 1.5, more preferably the pKa value of the buffer to be used plus or minus 1.0, and even more preferably the pKa value of the buffer to be used plus or minus 0.5. The content of the buffer only needs to be such an amount that the concentration of the buffer in the reaction liquid at the time of labeling of the chelated targeting agent with the radioactive metal is 2 mmol/L or more and 1,000 mmol/L or less, and is such an amount that the concentration of the buffer in the reaction liquid is preferably 10 mmol/L or more and 500 mmol/L or less, more preferably 50 mmol/L or more and 250 mmol/L or less.

A person skilled in the art could set the amount of the radioactive metal-containing solution to be used depending on a product design and appropriately set the amount of the buffer in accordance with the amount of the radioactive metal-containing solution.

A pharmacologically acceptable additional additive may be appropriately mixed in the composition of the present invention. As the additive, the composition of the present invention may further comprise, for example, an excipient, a surfactant, a pH adjuster, an isotonic agent, or a stabilizer.

Examples of the excipient include: sugar alcohols, such as erythritol, mannitol, xylitol, and sorbitol; sugars, such as white soft sugar, powdered sugar, lactose, sucrose, trehalose, and glucose; cyclodextrins, such as α-cyclodextrin, β-cyclodextrin, γ-cyclodextrin, hydroxypropyl-β-cyclodextrin, and sulfobutylether-β-cyclodextrin sodium salt; celluloses, such as crystalline cellulose and microcrystallinecellulose; and starches, such as corn starch, potato starch, and pregelatinized starch.

Examples of the surfactant include sodium lauryl sulfate, sodium dioctyl sulfosuccinate, polysorbate, and polyoxyethylene hydrogenated castor oil.

Examples of the pH adjuster include hydrochloric acid and sodium hydroxide. The pH adjuster can be used together with the buffer to adjust a pH.

Examples of the isotonic agent include sodium chloride, glucose, mannitol, and glycerin.

Examples of the stabilizer include ascorbic acid, benzyl alcohol, gentisic acid, α-thioglycerol, povidone, and ethanol.

Those additives may be used alone or in combination thereof. The blending amounts thereof are not particularly limited, and the additives may be appropriately blended so as to exhibit their effects sufficiently depending on purposes.

In the composition of the present invention, the chelated targeting agent and the buffer may be stored in the same vessel or in separate vessels, but are preferably stored in the same vessel. In the case of a composition in which the chelated targeting agent and the buffer are stored in the same vessel, a radioactive metal-labeled chelated targeting agent can be prepared only by mixing the composition and the radioactive metal. In a medical setting, it is preferred that an operation be as simple as possible from the viewpoint of preventing an erroneous operation. In the case of a composition in which the chelated targeting agent and the buffer are stored in separate vessels, it is appropriate to mix the chelated targeting agent and the buffer with each other, and then mix the radioactive metal therewith, to mix the chelated targeting agent and the radioactive metal with each other, and then mix the buffer therewith, or to mix the buffer and the radioactive metal with each other, and then mix the chelated targeting agent therewith, but it is preferred to mix the chelated targeting agent and the buffer with each other, and then mix the radioactive metal therewith. When the chelated targeting agent and the radioactive metal are mixed first, there is a risk in that the chelated targeting agent and the radioactive metal are brought into contact with each other without adjustment of a pH, and hence another reaction proceeds. Alternatively, when the buffer and the radioactive metal are mixed first, there is a risk in that a medium is adjusted to a neutral side, and the radioactive metal is precipitated as a hydroxide.

In addition, the composition of the present invention may be a composition further comprising, in addition to the chelated targeting agent and the buffer, the radioactive metal. Such composition means a kit in which all materials required for preparing an effective component of a radiopharmaceutical are provided as a set. The chelated targeting agent and the radioactive metal are often provided from separate entities, but it is convenient for a user that the chelated targeting agent and the radioactive metal be provided together as a set. However, the radioactive metal and the chelated targeting agent need to be stored under the state in which the radioactive metal and the chelated targeting agent are prevented from being brought into contact with each other. The radioactive metal and the chelated targeting agent are preferably stored in separate vessels.

A combination of: (A) the radioactive metal; (B) the chelated targeting agent; and (C) the buffer (specifically, a mixture of: a complex between the radioactive metal and the chelated targeting agent; and the buffer) is useful as a drug for diagnosis or treatment of a disease targeted by the chelated targeting agent. Here, the disease targeted by the drug for diagnosis or treatment is determined by the targeting moiety. For example, when the targeting moiety is an anti-CDH3 antibody, the disease is: an epithelial cancer, such as throat cancer, larynx cancer, tongue cancer, lung cancer, breast cancer, esophageal cancer, stomach cancer, colon cancer, uterus cancer, ovarian cancer, liver cancer, pancreas cancer, gallbladder cancer, kidney cancer, prostate cancer, malignant melanoma, or thyroid cancer; or a non-epithelial cancer, such as osteosarcoma, chondrosarcoma, rhabdomyosarcoma, leiomyosarcoma, liposarcoma, angiosarcoma, fibrosarcoma, leukemia, malignant lymphoma, or myeloma.

When the composition of the present invention is used as the drug for treatment, its administration route is generally a parenteral administration route. The composition of the present invention is administered, for example, through an injection (e.g., a subcutaneous injection, an intravenous injection, an intramuscular injection, or an intraperitoneal injection) or administered transdermally, transmucosally, transnasally, or transpulmonarily. A dose as the drug for treatment varies depending on, for example, the symptom, the administration route, the weight, and the age of a patient, but for example, a single dose for an adult is preferably from 37 MBq to 3,700 MBq.

A method of producing a radioactive metal-labeled chelated targeting agent may be performed, for example, as described below. When the radioactive metal and the chelated targeting agent are mixed in the presence of the buffer, the radioactive metal and the chelated targeting agent form a complex, and thus a radioactive metal-labeled chelated targeting agent can be produced. As described above, a method of mixing those components varies depending on the storage state of the chelated targeting agent and the buffer. That is, the chelated targeting agent and the buffer may be stored in the same vessel or in separate vessels, but are preferably stored in the same vessel. In the case of a composition in which the chelated targeting agent and the buffer are stored in the same vessel, the radioactive metal-labeled chelated targeting agent can be prepared only by mixing the composition and the radioactive metal. In the case of a composition in which the chelated targeting agent and the buffer are stored in separate vessels, it is appropriate to mix the chelated targeting agent and the buffer with each other, and then mix the radioactive metal therewith, to mix the chelated targeting agent and the radioactive metal with each other, and then mix the buffer therewith, or to mix the buffer and the radioactive metal with each other, and then mix the chelated targeting agent therewith, but it is preferred to mix the chelated targeting agent and the buffer with each other, and then mix the radioactive metal therewith.

EXAMPLES

Next, the present invention is described in further detail byway of Examples, but the present invention is not limited thereto.

1. Evaluation of Buffer

Tartaric acid, maleic acid, succinic acid, histidine, glutamic acid, benzoic acid, citric acid, 2-morpholinoethanesulfonic acid, and lactic acid were each selected as a buffer, and a buffering capacity and a labeling yield in a labeling reaction of a chelated targeting agent with $^{90}Y$ were examined. Acetic acid was examined simultaneously as a control.

A buffer solution was obtained by mixing an aqueous solution containing each of the buffers and an aqueous solution containing a conjugate acid or a conjugate base thereof or mixing the aqueous solution containing each of the buffers and an aqueous solution of hydrochloric acid or sodium hydroxide to adjust a pH of the buffer solution to 5.5.

DOTA-PPAT-052-28c described in Patent Literature 1 serving as a DOTA-anti-CDH3 antibody was used as a chelated targeting agent. DOTA-PPAT-052-28c was prepared as an antibody buffer solution in which DOTA-PPAT-052-28c was dissolved in the buffer solution at 2.5 mg/mL or 5 mg/mL.

DOTA-PPAT-052-28c was mixed with a $^{90}YCl_3$ solution (0.04 mol/L hydrochloric acid: manufactured by Cisbio Co., Ltd.) in the presence of the buffer to be labeled with $^{90}Y$. The labeling yield was confirmed as described below. A labeling reaction liquid was diluted with an aqueous solution containing DTPA having a chelating ability to $^{90}Y$, and an aliquot thereof was subjected to spotting on a thin-layer chromatography strip (manufactured by Biodex, Tec-Control Chromatography 150-771) and development with saline. After that, the labeling yield was confirmed with a radiochromanizer (manufactured by raytest, RITA). On the thin-layer chromatography strip, DOTA-PPAT-052-28c labeled with $^{90}Y$ remained at the origin, and unreacted $^{90}Y$ formed a complex with DTPA and was developed at the solvent front.

Evaluation of Tartaric Acid, Maleic Acid, and Succinic Acid

100 μL of an antibody buffer solution having a concentration shown in Table 1 and 38 μL of a $^{90}YCl_3$ solution were mixed with each other and subjected to a reaction at 40° C. for 15 minutes. After the reaction, the labeling yield was calculated by thin-layer chromatography. In addition, 1,000 μL of the buffer solution and 382 μL of 0.04 mol/L hydrochloric acid were mixed with each other and measured for a pH.

TABLE 1

| | Buffer solution | Concentration of buffer (mmol/L) |
|---|---|---|
| Comparative Example 1 | Sodium acetate buffer solution | 125 |
| Test Example 1 | Sodium tartrate buffer solution | 125 |
| Test Example 2 | Sodium tartrate buffer solution | 12.5 |
| Test Example 3 | Sodium maleate buffer solution | 125 |
| Test Example 4 | Sodium maleate buffer solution | 12.5 |
| Test Example 5 | Sodium succinate buffer solution | 125 |
| Test Example 6 | Sodium succinate buffer solution | 12.5 |

The results are shown in Table 2.

It was revealed that the buffer solutions were each able to exhibit a buffering capacity comparable to that of the sodium acetate buffer solution when having a concentration of 125 mmol/L. However, the sodium tartrate buffer solution had a low labeling yield despite the fact that a pH appropriate for the labeling reaction was achieved. This suggests that tartaric acid disturbs the labeling reaction with $^{90}Y$. The sodium maleate buffer solution and the sodium succinate buffer solution were each able to achieve a labeling yield comparable to that of the sodium acetate buffer solution.

TABLE 2

| | pH after mixing | Labeling yield (%) |
|---|---|---|
| Comparative Example 1 | 5.1 | 99.4 |
| Test Example 1 | 4.7 | 1.8 |
| Test Example 2 | 3.2 | 1.0 |
| Test Example 3 | 5.2 | 97.3 |
| Test Example 4 | 2.2 | 0.1 |
| Test Example 5 | 5.3 | 95.6 |
| Test Example 6 | 3.8 | 80.9 |

Evaluation of Histidine, Glutamic Acid, Benzoic Acid, and Maleic Acid

An antibody buffer solution shown in Table 3 and a $^{90}YCl_3$ solution were mixed at a ratio of 50:41 and subjected to a reaction at 40° C. for 15 minutes. After the reaction, the labeling yield was calculated by thin-layer chromatography. The antibody buffer solution shown in Table 3 and 0.05 mol/L hydrochloric acid were mixed at a ratio of 50:41 and measured for a pH.

TABLE 3

| | Antibody buffer solution | Concentration of buffer (mmol/L) |
|---|---|---|
| Comparative Example 2 | Sodium acetate buffer solution | 250 |
| Test Example 7 | Histidine buffer solution | 200 |
| Test Example 8 | Sodium glutamate buffer solution | 250 |
| Test Example 9 | Sodium benzoate buffer solution | 250 |
| Test Example 10 | Sodium maleate buffer solution | 200 |

The results are shown in Table 4.

It was revealed that the sodium glutamate buffer solution, the sodium benzoate buffer solution, and the sodium maleate buffer solution were each able to exhibit a buffering capacity comparable to that of the sodium acetate buffer solution. However, the sodium glutamate buffer solution had a low labeling yield despite the fact that a pH appropriate for the labeling reaction was achieved. This suggests that glutamic acid disturbs the labeling reaction with $^{90}Y$. The sodium benzoate buffer solution and the sodium maleate buffer solution were each able to achieve a labeling yield comparable to that of the sodium acetate buffer solution.

In addition, it was revealed that the histidine buffer solution did not have a sufficient buffering capacity at a concentration of Test Example 7.

TABLE 4

| | pH after mixing | Labeling yield (%) |
|---|---|---|
| Comparative Example 2 | 4.9 | 99.5 |
| Test Example 7 | 1.9 | 0.1 |
| Test Example 8 | 4.8 | 22.2 |
| Test Example 9 | 4.6 | 98.8 |
| Test Example 10 | 5.1 | 97.1 |

Evaluation of Citric Acid, 2-Morpholinoethanesulfonic Acid, and Lactic Acid

An antibody buffer solution shown in Table Sand a $^{90}YCl_3$ solution were mixed at a ratio of 50:41 and subjected to a reaction at 40° C. for 20 minutes. After the reaction, the labeling yield was calculated by thin-layer chromatography. The antibody buffer solution shown in Table 5 and 0.05 mol/L hydrochloric acid were mixed at a ratio of 50:41 and measured for a pH.

TABLE 5

| | Antibody buffer solution | Concentration of buffer (mmol/L) |
|---|---|---|
| Comparative Example 3 | Sodium acetate buffer solution | 250 |
| Test Example 11 | Sodium citrate buffer solution | 250 |
| Test Example 12 | 2-Morpholinoethanesulfonic acid buffer solution | 250 |
| Test Example 13 | Lactic acid buffer solution | 250 |

The results are shown in Table 6.

It was revealed that the buffer solutions were each able to exhibit a buffering capacity comparable to that of the sodium acetate buffer solution. However, the sodium citrate buffer solution and the lactic acid buffer solution each had a low labeling yield despite the fact that a pH appropriate for the labeling reaction was achieved. This suggests that citric acid and lactic acid each disturb the labeling reaction with $^{90}Y$. The 2-morpholinoethanesulfonic acid buffer solution was able to achieve a labeling yield comparable to that of the sodium acetate buffer solution.

TABLE 6

| | pH after mixing | Labeling yield (% ) |
|---|---|---|
| Comparative Example 3 | — | 99.3 |
| Test Example 11 | 5.5 | 0.2 |
| Test Example 12 | 4.3 | 99.4 |
| Test Example 13 | 4.3 | 4.3 |

2. Preparation of Freeze-Dried Formulation and Labeling with $^{90}Y$

Of the buffers each exhibiting a buffering capacity and a labeling yield comparable to those of the acetate buffer, benzoic acid was selected to prepare a freeze-dried formulation. Moreover, labeling with $^{90}Y$ was performed through use of the freeze-dried formulation.

1.4 mL of a 250 mmol/L sodium benzoate buffer solution containing DOTA-PPAT-052-28c at 5 mg/mL and trehalose at 100 mg/mL was freeze-dried under the conditions shown in Table 7 to yield a freeze-dried formulation in a white cake form.

Next, labeling with $^{90}Y$ was performed through use of the freeze-dried formulation. 1.4 mL of water for injection was added to the cake having been generated (Test Example 14). In addition, a 250 mmol/L sodium acetate buffer solution containing DOTA-PPAT-052-28c at 5 mg/mL was used as a control (Comparative Example 4). Each of those antibody solutions and a $^{90}YCl_3$ solution were mixed at a ratio of 50:41 and subjected to a reaction at 40° C. for 15 minutes. After the reaction, the labeling yield was calculated by thin-layer chromatography.

TABLE 7

| | Temperature (° C.) | Time (hour(s):minute(s)) |
|---|---|---|
| Segment 1 | −40 | 16:00 |
| Segment 2 | −35 | 0:40 |
| Segment 3 | −25 | 0:40 |
| Segment 4 | −10 | 10:20 |
| Segment 5 | 0 | 2:20 |
| Segment 6 | 10 | 2:20 |
| Segment 7 | 20 | 5:20 |

The results are shown in Table 8.

The 250 mmol/L sodium benzoate buffer solution was able to achieve a labeling yield comparable to that of the sodium acetate buffer solution even when having been freeze-dried. This indicates that the benzoate buffer does not sublimate even through a freeze-drying step and can maintain a sufficient buffering capacity at the time of its use, and is suitable as a buffer for a freeze-dried formulation.

TABLE 8

| | Labeling yield (%) |
|---|---|
| Comparative Example 4 | 98.5 |
| Test Example 14 | 99.2 |

INDUSTRIAL APPLICABILITY

The composition of the present invention is useful for production of a radioactive metal-labeled chelated targeting agent because the buffer contained in the composition can exhibit a pH buffering action without disturbing a reaction between the radioactive metal and the chelated targeting agent.

The invention claimed is:

1. A kit, comprising:

(a) a chelated targeting agent comprising a conjugate of a chelate group having a DOTA structure and an anti-CDH3 antibody targeting moiety;

(b) at least one buffer selected from the group consisting of benzoic acid, maleic acid, and salts thereof; and (c) an instruction describing preparing a radioactive metal-labeled chelated targeting agent by mixing a mixture of the chelated targeting agent and the buffer with a radioactive metal selected from the group consisting of $^{90}Y$ and $^{177}Lu$.

2. A kit, comprising:

(a) a chelated targeting agent comprising a conjugate of a chelate group comprising a DOTA structure and an anti-CDH3 antibody targeting moiety;

(b) at least one compound selected from the group consisting of benzoic acid, maleic acid, a conjugate base of benzoic acid, a conjugate base of maleic acid, a mixture of benzoic acid and a conjugate base of benzoic acid and a mixture of maleic acid and a conjugate base of maleic acid; and (c) an instruction describing preparing a radioactive metal-labeled chelated targeting agent by mixing a mixture of the chelated targeting agent and the compound with a radioactive metal selected from the group consisting of $^{90}Y$ and $^{177}Lu$.

3. A kit, comprising:

(a) a chelated targeting agent comprising a conjugate of a chelate group having a DOTA structure and an anti-CDH3 antibody targeting moiety;

(b) at least one buffer selected from the group consisting of benzoic acid, maleic acid, and salts thereof; and (c) a radioactive metal selected from the group consisting of $^{90}Y$ and $^{177}Lu$, wherein the radioactive metal is in a separate vessel from a vessel containing the chelated targeting agent and the buffer.

4. A kit, comprising:

(a) a chelated targeting agent comprising a conjugate of a chelate group comprising a DOTA structure and an anti-CDH3 antibody targeting moiety;

(b) at least one compound selected from the group consisting of benzoic acid, maleic acid, a conjugate base of benzoic acid, a conjugate base of maleic acid, a mixture of benzoic acid and a conjugate base of benzoic acid and a mixture of maleic acid and a conjugate base of maleic acid; and (c) a radioactive metal selected from the group consisting of $^{90}Y$ and $^{177}Lu$, wherein the radioactive metal is in a separate vessel from a vessel containing the chelated targeting agent and the compound.

5. The kit of claim 1, wherein the mixture of the chelated targeting agent and the buffer is freeze-dried.

6. The kit of claim 2, wherein the mixture of the chelated targeting agent and the compound is freeze-dried.

7. The kit of claim 3, wherein the chelated targeting agent and the buffer in the vessel are freeze-dried.

8. The kit of claim 4, wherein the chelated targeting agent and the compound in the vessel are freeze-dried.

9. The kit of claim 1, wherein the buffer is selected from the group consisting of benzoic acid and salts thereof.

10. The kit of claim 2, wherein the compound is selected from the group consisting of benzoic acid, a conjugate base of benzoic acid, and a mixture of benzoic acid and a conjugate base of benzoic acid.

11. The kit of claim 3, wherein the buffer is selected from the group consisting of benzoic acid and salts thereof.

12. The kit of claim 4, wherein the compound is selected from the group consisting of benzoic acid, a conjugate base of benzoic acid, and a mixture of benzoic acid and a conjugate base of benzoic acid.

* * * * *